(12) United States Patent
Mongeon et al.

(10) Patent No.: US 9,662,501 B2
(45) Date of Patent: May 30, 2017

(54) BI-VENTRICULAR VENTRICULAR CAPTURE MANAGEMENT IN CARDIAC RESYNCHRONIZIATION THERAPY DELIVERY DEVICES

(71) Applicant: Medtronic, Inc., Minneapolis, MN (US)

(72) Inventors: Luc R Mongeon, Minneapolis, MN (US); Karen J Kleckner, New Brighton, MN (US); John C Rueter, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 730 days.

(21) Appl. No.: 13/626,490

(22) Filed: Sep. 25, 2012

(65) Prior Publication Data

US 2013/0090702 A1    Apr. 11, 2013

Related U.S. Application Data

(63) Continuation of application No. 11/312,874, filed on Dec. 20, 2005, now abandoned.

(60) Provisional application No. 60/637,633, filed on Dec. 20, 2004.

(51) Int. Cl.
| | |
|---|---|
| *A61N 1/37* | (2006.01) |
| *A61N 1/365* | (2006.01) |
| *A61N 1/362* | (2006.01) |
| *A61N 1/368* | (2006.01) |

(52) U.S. Cl.
CPC ....... *A61N 1/36592* (2013.01); *A61N 1/3627* (2013.01); *A61N 1/3684* (2013.01); *A61N 1/371* (2013.01)

(58) Field of Classification Search
USPC .......................................................... 607/28
See application file for complete search history.

(56) References Cited

U.S. PATENT DOCUMENTS

| | | | |
|---|---|---|---|
| 4,428,378 A | 1/1984 | Anderson et al. | |
| 5,052,388 A | 10/1991 | Sivula et al. | |
| 6,512,953 B2 * | 1/2003 | Florio et al. | 607/28 |

(Continued)

*Primary Examiner* — Rex R Holmes
(74) *Attorney, Agent, or Firm* — Carol F. Barry

(57) ABSTRACT

The present invention provides a technique for verifying pacing capture of a ventricular chamber, particularly to ensure desired delivery of a ventricular pacing regime (e.g., "CRT"). The invention also provides ventricular capture management by delivering a single ventricular pacing stimulus and checking inter-ventricular conduction during a temporal window to determine if the stimulus captured. If a loss-of-capture LOC) signal results from the capture management testing, then the applied pacing pulses are modified and the conduction test repeated. If LOC, an alert message can issue. Other aspects include: use of a trend of A-RV/LV and LV-RV timing intervals to monitor changes in the patient's heart conduction properties; bi-ventricular verification test and search—while still pacing BiV by detecting latent sense; single-V pacing threshold search, use of timing of sense in other V chamber to establish capture and LOC windows; (iv) use of a premature V pace rather than short AV interval if VV cannot be discriminated from AV; (v) option to run a threshold search only if the Bi-ventricular verification test fails.

32 Claims, 4 Drawing Sheets

(56) References Cited

U.S. PATENT DOCUMENTS 6,772,005 B2 8/2004 Casavant et al.
2002/0062139 A1 5/2002 Ding

* cited by examiner

BI-VENTRICULAR VENTRICULAR CAPTURE MANAGEMENT IN CARDIAC RESYNCHRONIZIATION THERAPY DELIVERY DEVICES

FIELD OF THE INVENTION

The invention pertains to cardiac pacing systems and relates to apparatus and methods for triggering automatic verification of pacing capture of ventricular chambers and for managing pacing therapy delivery to ensure continued pacing capture. In particular, the invention relates to verification of pacing capture for both ventricular chambers during bi-ventricular pacing, including various forms of cardiac resynchronization therapy (CRT) delivery, such uni-ventricular, fusion-type CRT delivery.

BACKGROUND OF THE INVENTION

Cardiac resynchronization cardiac pacing devices operate by either delivering pacing stimulus to both ventricles or to one ventricle with the desired result of a more or less simultaneous mechanical contraction and ejection of blood from the ventricles. However, due to a number of factors for a variety of patients such cardiac pacing systems may not always effectively delivery CRT. For example, varying capture thresholds, pacing lead and/or electrode migration or dislodgement, time required for appropriate signal processing, confounding conduction delays or conduction blockages, diverse electrode placement locations, and the like.

In either form of CRT delivery, whether fusion-based or the more traditional bi-ventricular stimulation, confirming that pacing stimulus captures each paced ventricle is a very important clinical issue so that the desired benefits of the CRT are in fact delivered to a patient.

Assuming that the reader is familiar with bi-ventricular pacing, the following should provide additional insight into the importance of capture detection in a fusion-based bi-ventricular pacing engine. One premise underlying fusion-based pacing is the notion that a fusion-based evoked left ventricular (LV) depolarization enhances stroke volume in hearts where the right ventricle (RV) depolarizes first. This is commonly due to intact atrio-ventricular (AV) conduction to the RV of a preceding intrinsic or evoked atrial depolarization wave front, and wherein the AV conducted depolarization of the LV is unduly delayed. The fusion depolarization of the LV is attained by timing the delivery of the LV pace (LVp) pulse to follow the intrinsic depolarization of the RV but to precede the intrinsic depolarization of the LV. Specifically, an RV pace (RVp) pulse is not delivered due to the inhibition of the RVp event upon the sensing of RV depolarization (RVs), allowing natural propagation of the wave front and depolarization of the intraventricular septum, while an LVp pulse is delivered in fusion with the RV depolarization. For supporting mode switches to alternate pacing modalities, fusion-based CRT delivery engines typically include at least one electrode in each ventricle which allows such engines to be used in conjunction with the present invention, as will be apparent upon review of the following written description and drawings of the invention.

Left ventricular capture in particular is a clinical issue with present-generation (and foreseeable) CRT systems, due to acknowledged difficulty of maintaining stable lead situation in the cardiac venous anatomy. Since CRT delivery becomes ineffective (possibly even deleterious) if LV capture is lost, diagnosis of dislodgment and maintenance of capture are high priorities.

Cardiac Resynchronization Therapy (CRT) devices have been shown to improve quality of life (QOL), exercise capacity and New York Heart Association (NYHA) heart failure class. The NYHA rating varies from Class I to Class IV, as follows: Class I: patients with no limitation of activities; they suffer no symptoms from ordinary activities. Class II: patients with slight, mild limitation of activity; they are comfortable with rest or with mild exertion. Class III: patients with marked limitation of activity; they are comfortable only at rest. Class IV: patients who should be at complete rest, confined to bed or chair; any physical activity brings on discomfort and symptoms occur at rest.

Currently approved CRT devices incorporate bi-ventricular pacing technology with simultaneous pacing in the right ventricle (RV) and the left ventricle (LV). Since the devices are implanted essentially only to provide continuous bi-ventricular pacing therapy, it is imperative that each pacing pulse stimulus delivered to the two LV and RV provide an evoked response (i.e., each stimulus delivered to a ventricle "captures" the ventricle). Thus, if electrodes disposed in electrical communication with a ventricle rapidly sense depolarization wavefronts a control sequence for the pacing engine will inhibit ventricular pacing. For example, such a situation occurs during rapidly conducted atrial fibrillation (AF). When bi-ventricular pacing is inhibited the patient's symptoms of heart failure return, and can sometimes even worsen as compared to their pre-implant status. Similarly, if one of the pacing sites loses capture (e.g., the LV) the subsequent RV-only pacing will prevent the patient from receiving the intended benefit of CRT delivery. To that end the inventors have addressed a need in the art regarding capture verification in heart failure devices, such as bi-ventricular CRT devices that indicates when capture is occurring in both the LV and the RV.

Presently, the only somewhat similar diagnostic available in CRT devices is percent-ventricular pacing (% Vpacing), which indicates the percentage of time bi-ventricular pacing therapy is being delivered; however, a limitation of the % Vpacing metric is that bi-ventricular pacing may be "occurring" close to 100% of the time but the LV chamber may not be captured at all. Currently, cardiac device specialists assess LV capture acutely during office visits by looking at the morphology of an electrogram (EGM) or by temporarily setting pacing to RV-only and LV-only pacing. Current state of the art pacemakers (e.g., the Kappa® brand family of pacemakers provided by Medtronic, Inc.) incorporate ventricular capture management algorithms. However, such algorithms require specific circuitry and sensing capabilities to be able to perform this function that are not currently available in the CRT products. Also, the feasibility of this technology for LV capture management has yet to be established. The present invention advantageously contributes to both capture verification and management.

Previously others addressed issues related to capture management; for example, Ventricular Capture Management (VCM) has been successfully implemented in the Kappa® 700 dual-chamber pacemaker sold by Medtronic, Inc. by measuring evoked responses on the bipolar pair of electrodes in the right ventricle (RV). In this device the pacing output energy is monitored and automatically adjusted as required by the patient. This pacing threshold search (PTS) measures the rheobase and chronaxie of the current pacing threshold. The following can be used to determine rheobase and chronaxie: 1—determine the rheobase, which is the minimum Stimulus Strength that will produce a response (his is the voltage to which the Strength-Duration curve asymptotes). Step 2—calculate 2×rheobase and step 3—determine chronaxie, which is the Stimulus Duration that yields a response when the Stimulus Strength is set to exactly 2×rheobase.

Then, a pulse width and amplitude safety margin is calculated and the output of the device is set to that new value. The PTS is conducted on a programmable periodic basis, commonly set up to measure the thresholds once a day (typically at night).

Currently in the bi-ventricular pacing CRT devices like the InSync® family of implantable pulse generators, including ICDs), no capture verification or threshold management scheme exists. Instead, pacing thresholds are manually measured at the right ventricular and the left ventricular pacing sites. The site with the highest pacing threshold requirement dictates the programmed output of the device to assure proper capture at both ventricular sites for devices with a single ventricular pacing stimulus energy output.

A need therefore exists in the art to effectively chronically deliver ventricular pacing therapies (including CRT) to patients who might not otherwise receive the full benefit of such therapies.

SUMMARY

Among other contributions to the art, the present invention addresses the issues identified above of not providing adequate metrics (or diagnostics) to a physician regarding LV (and therefore bi-ventricular) capture. The invention addresses this significant need where capture management functionality is not available in a CRT device. According to the invention, the bi-ventricular capture management as described here measures and monitors pacing thresholds at each of pacing sites being used in CRT delivery while the patient is ambulatory. The ability to obtain the LV and RV thresholds and modulate these outputs helps assure greater likelihood of bi-ventricular capture. Such dual site capture is critical in order for a patient to benefit from CRT. Bi-ventricular capture verification and capture management is also an important element to enable remote follow-up (e.g., via a patient management network or the like) and to provide a triage tool for understanding whether worsening heart failure is due to a device pacing-capture problem versus a manifestation of worsening heart failure. The clinically important aspect of managing pacing capture thresholds in these patients is that an HF decompensation event that might have been related to bi-ventricular capture problems are eliminated due to the dynamic nature of the (left-sided) pacing stimulus output energy. In the event that the capture detection and management scheme detects a situation of failed LV capture (e.g., left side lead dislodgement), a clinician or physician can be notified via a network such as the Medtronic CareLink® network alert system utilizing e-mail, fax, phone calls, paging networks and the like.

Currently no bi-ventricular capture management scheme has been implemented in any pacing therapy delivery device, such as an IPG. As stated hereinabove, the advantages are both from a clinician ease-of-use perspective, for example a clinically significant aspect of assuring CRT is being effectively delivered as planned, and a timesaving triage tool which would help identify left-lead issues that comprise a significant issue for patients who are scheduled to receive chronic CRT delivery.

Thus, at least on exemplary algorithm is described for rapid incorporation into next-generation CRT devices that actively performs LV capture verification and threshold test(s) on a daily (or other) basis with automatic retry and wireless communication of testing results, trends and the like (including any testing anomalies). The results of the test(s) can be stored and/or provided to the user, a clinician, or other entity. The results of the tests can be provided remotely or via a programming head at a next programmer-based session, as is known in the art. The data regarding LV capture can be used, for example, to record or demonstrate whether an intended CRT delivery is occurring and the amount of time or percentage that a patient in fact received CRT. If LV capture verification is NOT confirmed, in addition to the stored diagnostic metrics, a patient alert can be triggered to warn the patient (and/or a clinician) that the device is not functioning as intended and the patient should consider consulting a physician.

In one form of the invention, such a patent alert can be triggered on a remote patient management network (e.g., the Medtronic Medtronic CareLink® remote monitoring service for patients with Medtronic cardiac devices) to notify third parties of the lack of CRT delivery. This test and the resultant diagnostic metric values (e.g., percentage of actual CRT delivery in temporal terms, by the number of cardiac cycles with and without CRT delivery, or by time of day and the like) simply and accurately depicts actual CRT delivery. The values also provide assurance to the physician, patient and/or care-giver that the device is not only pacing in both ventricular chambers, but capturing, thereby providing maximal therapeutic benefit to the patient. The values also help in the early identification of a situation where, for some reason a pacing lead is not capturing in the associated ventricle thereby minimizing patient discomfort and restoration of the desired therapeutic regime. Also, a test according to the invention can be applied to verify RV capture and for in-office, easy-to-use acute confirmation of capture verification of the LV and RV. Multiple approaches can be used for measuring the pacing threshold at the left and right ventricular sites.

For example, evoked response measurement at each site: this involves measuring the pacing threshold using the evoked response approach previously used in the Kappa devices of Medtronic, Inc. The capture management feature provides automatic monitoring of ventricular pacing thresholds and automatic adjustment of amplitude and pulse width to maintain capture. When capture management is programmed to monitor only, the pacemaker periodically causes paces to be delivered (affecting pacemaker timing temporarily if necessary). The pacemaker then monitors the paces by changing first amplitude and then pulse width to find two points that lie on the strength duration curve that define the boundary between settings that capture and those that do not. How often the pacemaker performs this pacing threshold search is determined by the programmable Capture Test Frequency parameter. This parameter determines how often the pacing threshold search will be initiated and provides for retry if the test is delayed. When Capture Management is programmed to Adaptive, the pacemaker responds to monitoring by adapting ventricular amplitude and pulse width using the following programmable parameters:

Amplitude Margin and Pulse Width Margin—the pacemaker determined threshold multiplied by a selected safety factor.

Minimum Adapted Amplitude and Minimum Adapted Pulse Width—the lower limit to which Amplitude and Pulse Width can be set by the pacemaker during adaptation.

Acute Phase Days Remaining—time in days during which the pacemaker will not decrease output settings below the initially programmed settings. This parameter is used during the lead maturation period.

The LV threshold can thus be measured using evoked response as on the left side. Pacing threshold measurements using evoked responses can require that each pacing site be individually evaluated.

Another way to accomplish LVCM according to the invention involves intrinsic deflection detection at each site: According to this aspect of the invention uses the detection of an intrinsic deflection within a certain window that is generated from a pacing pulse at the other ventricular electrode. The advantage to using such an algorithmic approach is that it can be implemented on a pacing engine that has independent ventricular channels. This approach could be initiated via the device programmer or a remote monitor, such as the Medtronic CareLink network supported by Medtronic, Inc. So, for example, if a clinician wants to collect data on pacing thresholds they could readily access the data remotely.

Yet another technique according to the invention involves a hybrid of intrinsic at one site and evoked at the other: The use of the intrinsic deflection sensing on the one side only may provide an advantage as the evoked response sensing circuitry for the second site would be unnecessary.

Another aspect of the invention is that a variety of verification test protocols can be implemented that increase in aggressiveness if a prior test fails or is inconclusive. According to this aspect of the invention, a "level 1" verification test might only confirm that capture is occurring at the currently programmed settings. It could also evaluate if a sensed event can actually occur at each electrode to eliminate lead dislodgement as a reason for a failure to sense cardiac events. According to this level of verification, the pacing output channels would not be reprogrammed nor is any therapy delivery modified (e.g., no pacing mode switches).

Another somewhat indirect capture management technique involves periodic measurement of QRS durations and comparison between a prior duration wherein capture was confirmed. Such a comparison also provides some evidence of the state of heart failure and/or conduction defects of a patient.

Some applications of the invention without limitation include: (1) ambulatory, automatic LV capture verification; (2) ambulatory, automatic RV capture verification; (3) diagnostic data display on trends of capture performance; (4) alerts to clinics, physicians and patients when LV capture is suspect or lost; (5) in-office easy-to-use LV/RV capture verification testing; (6) automatic ambulatory LV and RV capture management (e.g., adjustment of pacing outputs to maintain capture); and (7) providing capture verification and/or pacing threshold search (PTS) testing with atrial-tracking and non-tracking modalities. The latter use can include aspects of the following: the present inventive method provides an effective avenue for providing device intelligence and automatic adjustment of operating parameters to ensure pacing capture of the ventricles (LV and/or RV). In the event that pacing capture is lost, or is suspect, the patient or a clinic (or clinician) can be notified and/or certain pacing or sensed parameters of the medical device stored and/or sent via telemetry to a remote location for later review. The stored parameters provide a clinician with diagnostic data for a patient that can be stored in a graphical format, histogram or the like for convenient review.

According to the present invention a ventricular pacing device (including CRT delivery devices) analyzes myocardial electrogram signals in one ventricle can be used to infer capture or loss-of-capture (LOC) of an earlier stimulus pulse in the same ventricle, on a continuous (every pacing cycle), aperiodic or periodic basis. Rather than using an evoked-response principle as has been the basis of capture detection in prior art systems, a principle employed via the present invention uses evidence of inter-ventricular conduction (i.e., from the opposite chamber) as evidence of LOC, since a non-capturing pacing stimulus will allow myocardial tissue to remain non-refractory and thus inter-ventricular wave-front propagation (i.e., conduction) and organized myocardial contractions to commence.

Using existing sense amplifiers and associated circuitry, simple and efficient signal analysis, and discrimination of the conducted signal of interest (from unwanted signals of cardiac activity such as T-waves, premature ventricular contractions, or "PVCs," far-field R-waves, and the like) can be enhanced as needed based on the timing the sensed signal, its magnitude or other morphology characteristics, as registered by suitable circuitry.

Ventricular sensing of intrinsic (not evoked) depolarization signal can thus be used to infer LOC, as a basis for diagnostic and auto-adjustment of stimulus output, in CRT or multi-site bradycardia therapy devices.

Other aspects of the invention include, without limitation, some or all of the following: (i) Use of a trend of A-RV/LV and LV-RV timing intervals to monitor changes in the patient's heart conduction properties; (ii) BiV verification test and search—verifying capture in RV and LV while still pacing BiV by looking for a latent sense following the BiV pace; (iii) single V pacing threshold search, use of timing of sense in other V chamber to establish capture and LOC windows; (iv) use of a premature V pace rather than short AV interval if VV cannot be discriminated from AV; (v) option to run a threshold search only if the Bi-ventricular verification test fails.

The foregoing and other aspects and features of the present invention will be more readily understood from the following detailed description of the embodiments thereof, when considered in conjunction with the drawings, in which like reference numerals indicate similar structures throughout the several views.

DETAILED DESCRIPTION OF THE ILLUSTRATED EMBODIMENTS

In the following detailed description, references are made to illustrative embodiments for carrying out methods of confirming pacing capture of ventricular pacing stimulation. It is understood that other embodiments may be utilized without departing from the scope of the invention. For example, the invention is disclosed in detail herein in the context of a bi-ventricular CRT delivery. In one form of the invention, a pacing regimen is modified to single-ventricle pacing therapy delivery wherein ventricular sensing in a first ventricle of a pacing stimulus delivered to a second ventricle is used to verify pacing capture in said first ventricular chamber. Thus, loss-of-capture (LOC) can be declared, verified or managed and one of several possible responses initiated. For example, the pacing pulse stimulus can be adjusted (e.g., modified pulse amplitude, pulse width, polarity, etc.), a pacing mode-switch can be implemented, and/or in relatively extreme cases a clinician can attempt to adjust the system, including electrode location, to improve pacing capture. A cardiac pacing apparatus, according to the invention, comprises a programmable implantable pulse generator (IPG) that can be operated as a dual- or triple-chamber pacing system having an AV synchronous operating mode for restoring upper and lower heart chamber synchronization and/or right and left atrial and/or ventricular chamber depolarization synchrony. A system according to the invention efficiently provides cardiac resynchronization therapy (CRT) with a single ventricular stimulus per cardiac cycle in a fusion-inducing CRT delivery or with a pair of synchronized bi-ventricular pacing stimulus per cardiac cycle.

The present invention provides enhanced hemodynamic performance for patients that benefit from CRT delivery due to various forms of heart failure, ventricular dysfunctions and/or ventricular conduction abnormalities. Pacing systems according to the present invention can also include rate responsive features and anti-tachyarrhythmia pacing and the like. In addition, a system according to the invention can include cardioversion and/or defibrillation therapy delivery.

Figure 1:
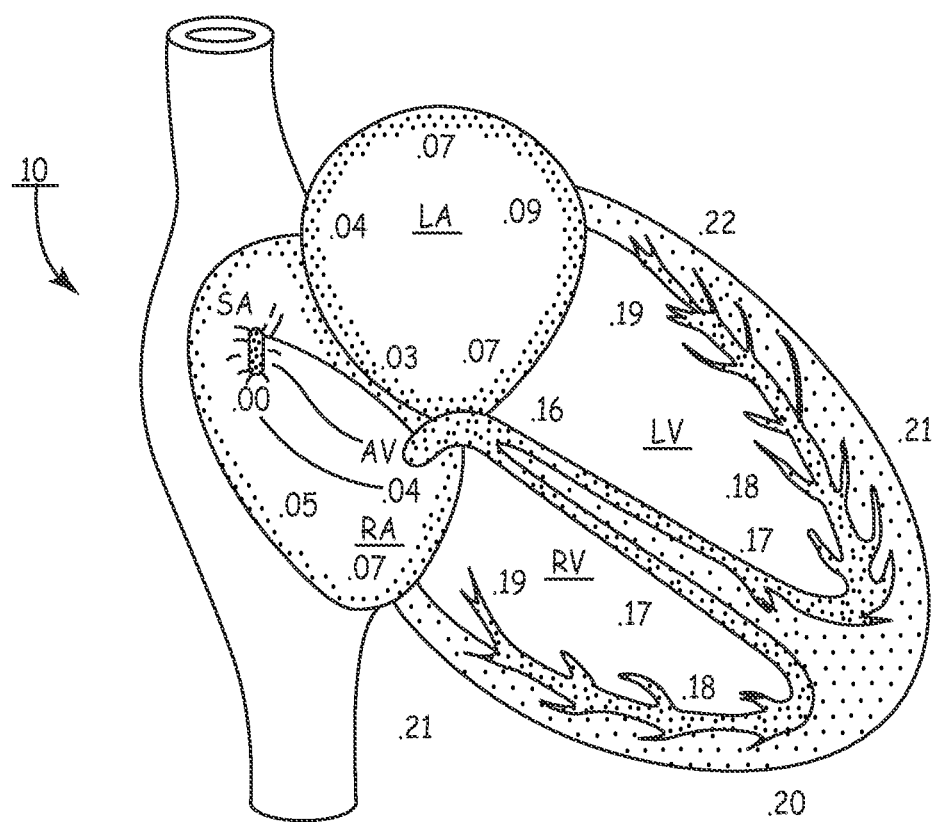
FIG. 1 is an illustration of transmission of a normal cardiac conduction system through which depolarization waves are propagated through the heart in a normal intrinsic electrical activation sequence.

In accordance with an aspect of the present invention, a method and apparatus is provided to mimic the normal depolarization-repolarization cardiac cycle sequence (nominally depicted in FIG. 1) and restore cardiac intra- and/or inter-ventricular synchrony between the RV and LV that contributes to adequate cardiac output related to the synchronized electromechanical performance of the RV and LV. The foregoing and other advantages of the invention are realized through confirmed delivery of cardiac pacing stimulation to the ventricles. For example, a number of physiologic factors can influence the ability of delivered pacing stimulus to capture a cardiac chamber. For instance, conduction delays through the A-V node and/or the His-Purkinje fibers, electrical conduction delay for sensing intra-cardiac events (from electrodes through threshold sensing circuitry of a medical device), electrical conduction delay for pacing therapy delivery circuitry, electro-mechanical delay associated with the delivery of a pace and the ensuing mechanical contraction, ischemic episodes temporarily tempering conduction pathways, myocardial infarction(s) zones, all can deleteriously impact cardiac conduction and thereby affect an operating pacing therapy delivery regime. Because the conduction status of a patient can vary over time and/or vary based on other factors such as heart rate, autonomic tone and metabolic status, the present invention provides a dynamically controllable resynchronization pacing modality.

According to the invention verification of capture can be triggered so that a desired amount of dual- or single-chamber (fusion-based) CRT delivery ensues. Some of the factors include, (i) completion of a pre-set number of cardiac cycles, (ii) pre-set time limit, (iii) loss of capture of a paced ventricle, (iv) physiologic response triggers (e.g., systemic or intra-cardiac pressure fluctuation, heart rate excursion, metabolic demand increase, decrease in heart wall acceleration, intra-cardiac electrogram morphology or timing, etc.) and/or (v) time of day, and the like. The present invention provides a cardiac pacing system that can readily compensate for the particular implantation sites of the pace/sense electrode pair operatively coupled to a ventricular chamber. When implemented in a triple-chamber embodiment, a pacing system according to the present invention can quickly mode-switch in the event that loss-of-capture (LOC) is declared.

Figure 2:
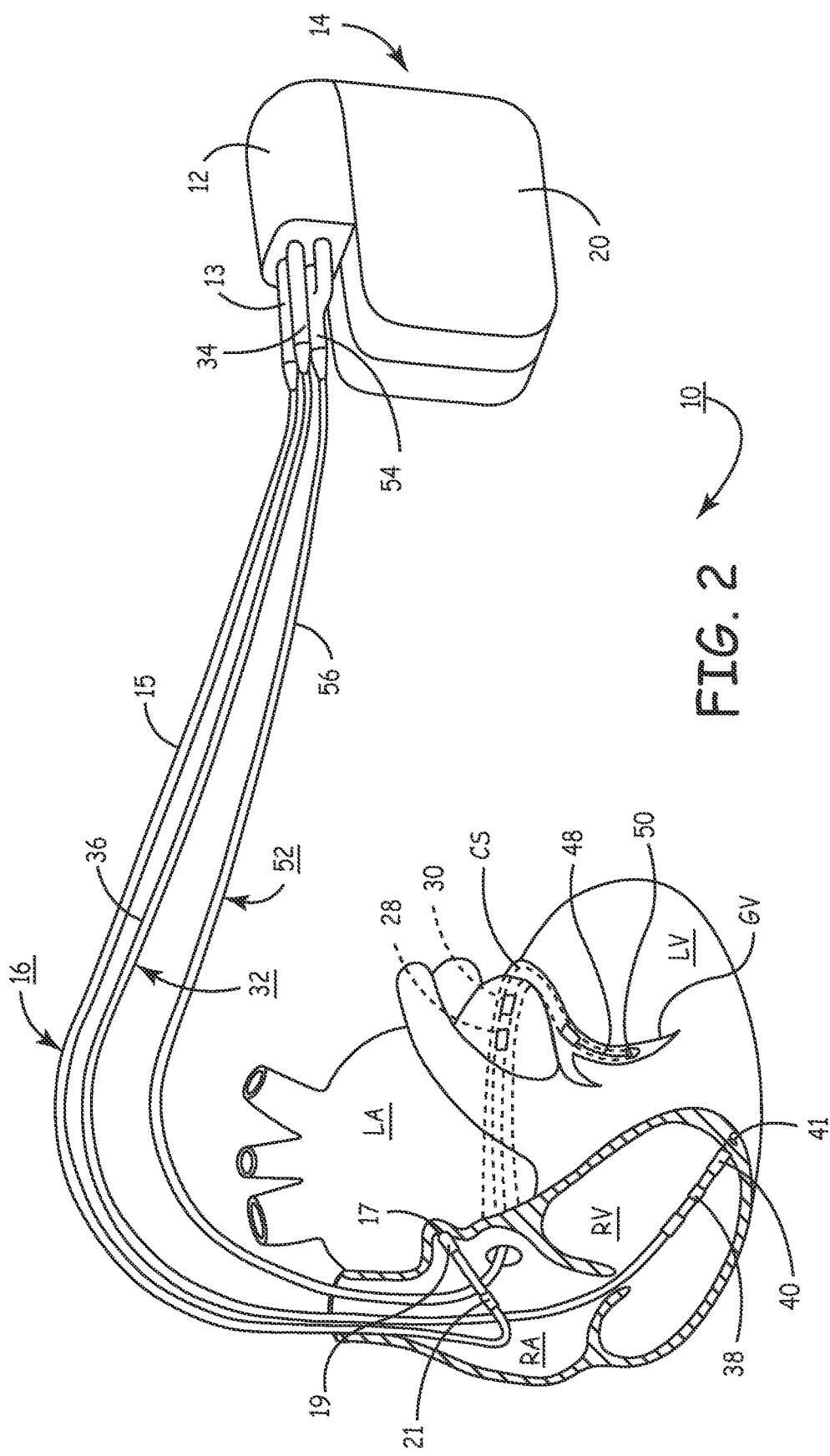
FIG. 2 is a schematic diagram depicting a three channel, atrial and bi-ventricular, pacing system for implementing the present invention.

FIG. 2 is a schematic representation of an implanted, triple-chamber cardiac pacemaker comprising a pacemaker IPG 14 and associated leads 16,32,52 in which the present invention may be practiced. The pacemaker IPG 14 is implanted subcutaneously in a patient's body between the skin and the ribs. The three endocardial leads 16,32,52 operatively couple the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals (e.g. far field R-waves). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. Also, as noted previously, multiple electrodes and/or leads may be deployed into operative communication with the relatively "late" depolarizing ventricle to pace at multiple sites with varying degrees of pre-excitation. In addition, mechanical and/or metabolic sensors can be deployed independent of, or in tandem with, one or more of the depicted leads. In the event that multiple pacing electrodes are operatively deployed into communication with a single chamber, a capture detection for each such electrode may be individually performed. That is, different pacing stimulus can be implemented for each discrete pacing location and said pacing stimulus delivery can thus be tuned for capture and/or conduction anomalies (e.g., due to infarct or ischemia or the like).

As depicted, a bipolar endocardial RA lead 16 passes through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

Further referring to FIG. 2, a bipolar, endocardial coronary sinus (CS) lead 52 is passed through a vein and the RA chamber of the heart 10, into the coronary sinus and then inferiorly in a branching vessel of the great cardiac vein to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein. In addition, while not depicted in FIG. 2 the atrial, ventricular, and/or CS-deployed pacing leads can couple to the exterior of a heart via a pericardial or epicardial attachment mechanism.

In a four chamber or channel embodiment, LV CS lead 52 bears proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching from the great vein (GV).

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND-_CAN electrode 20 or the ring electrodes 21 and 38, respectively for pacing and sensing in the LA and LV, respectively.

Figure 3:
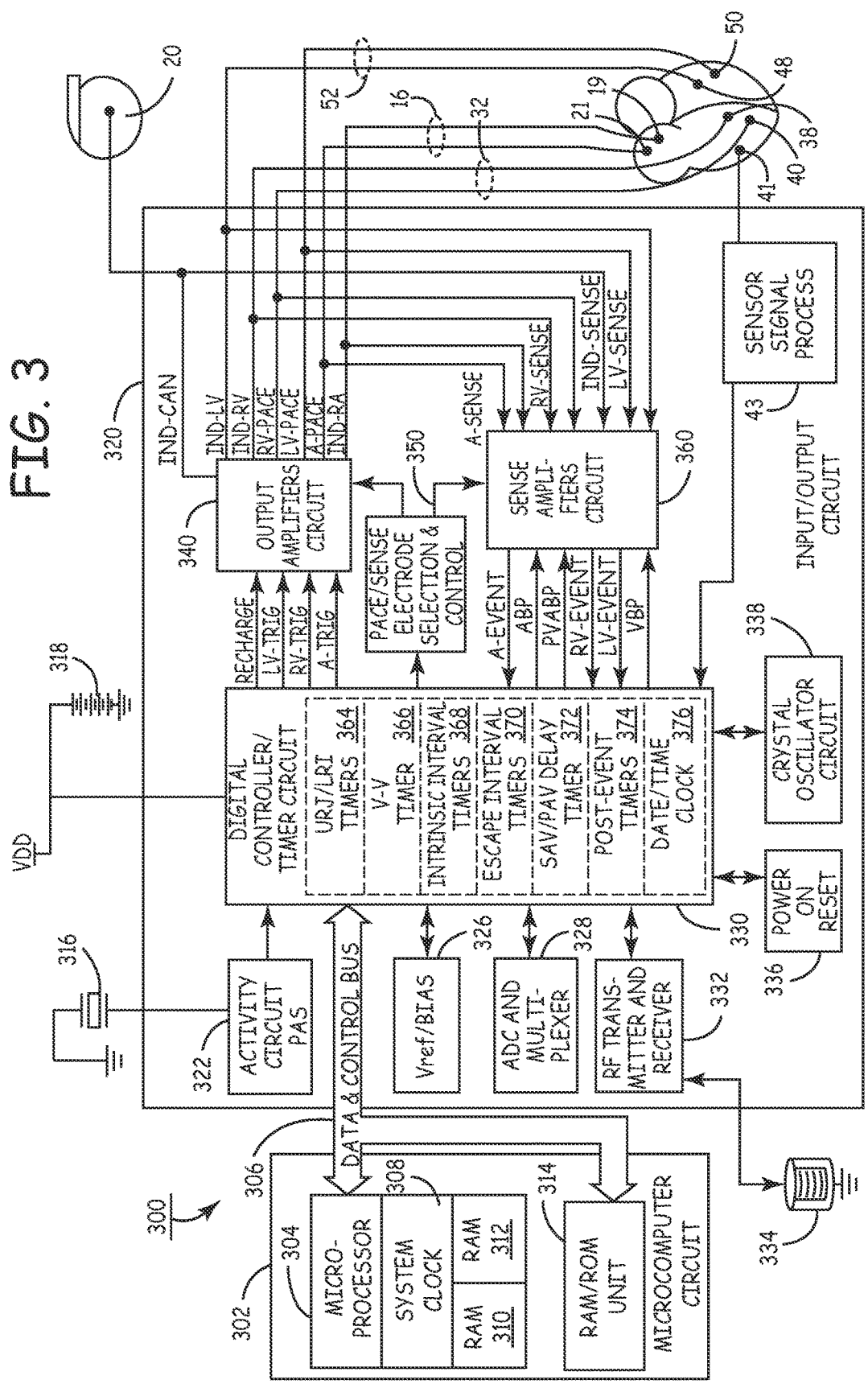
FIG. 3 is a simplified block diagram of one embodiment of IPG circuitry and associated leads employed in the system of FIG. 2 for providing three sensing channels and corresponding pacing channels that selectively functions in an energy efficient, single-pacing stimulus, ventricular pre-excitation pacing mode according to the present invention.

In this regard, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDD/R type known in the pacing art. In turn the sensor signal processing circuit 43 indirectly couples to the timing circuit 330 and via bus 306 to microcomputer circuitry 302. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and an associated RF transceiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 304 may also serve to define variable, operative AV delay intervals and the energy delivered to each ventricle.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay (or A-RVp delay) from a preceding A-EVENT or A-TRIG, a post-ventricular timer 374 for timing post-ventricular time periods, and a date/time clock 376.

According to the invention, the AV delay interval timer 372 is loaded with an appropriate delay interval for one ventricular chamber (i.e., either an A-RVp delay or an A-LVp delay) to time-out starting from a preceding A-PACE or A-EVENT. The interval timer 372 triggers pacing stimulus delivery, and can based on one or more prior cardiac cycles (or from a data set empirically derived for a given patient)

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse, if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in contemporary cardiac pacemakers for atrial and ventricular pacing and sensing. As is known, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Multiple approaches can be used for measuring the pacing threshold at the left and right ventricular sites according to the invention. For example, evoked response measurements at each pacing site. This approach involves continuing to measure the ventricular thresholds using the evoked response approach. According to this approach, each of the RV and LV thresholds are measured using an evoked response approach. That is, pacing threshold measurements using evoked responses generally require that each pacing site (e.g., each pacing stimulus vector, uni-polar and/or bi-polar, etc.) be individually evaluated. According to this approach, the pacing stimulus energy delivered to each ventricle can be iteratively reduced until LOC is declared. The LOC declaration can be obtained from temporal EGM signal traces, temporal ECG signal traces, mechanical sensors (e.g., accelerometer, fluid pressure sensor, and the like). Once LOC is declared the pacing stimulus energy can be increased to a chamber-capturing threshold. This threshold can be used chronically, although typically the chronic pacing energy is increased by a small, so-called safety margin so that capture is more likely to be maintained.

Another approach involves intrinsic deflection detection at each site wherein detection of an intrinsic deflection within a certain temporal window. The temporal window is generated from a pacing pulse using another ventricular electrode (or vector). The advantage to using such an evoked response algorithmic approach is that no need exists to Implement the evoked response detection circuitry on a new, or modified, device platform, and the features of the invention could be implemented on the future devices which have independent ventricular pacing circuitry and channels. This approach can also be used for a remote monitoring scheme both ambulatory (or at least at a patient's residence) or used in the office or clinic by a clinician that wants to measure pacing thresholds. The test could be initiated via the programmer or the Medtronic CareLink® network instruments developed and supported by Medtronic, Inc. In addition, a hybrid approach of both intrinsic threshold testing at one site and evoked response testing at the other involves use of intrinsic deflection sensing on one side only (i.e., LV or RV) can provide advantages since the evoked response sensing circuitry for the second side would be unnecessary. Moreover, both approaches at each site (or for each side, LV and RV) can be advantageously applied in order to cross check results or in the event that one technique is ineffective at one or both sites. The foregoing appears to represent a better approach—or the best of both—since it provides redundant systems for performing the same function.

As implied above, the use of multiple electrode locations could also be used to conduct the threshold tests and/or to monitor the intraventricular delay between two or more pacing sites. Such multiple electrodes can comprise an chronically implanted multi-polar pacing lead or an acute interventional procedure using an electrophysiology catheter, such as a decapolar diagnostic catheter. Such multipolar testing can be used to optimize CRT delivery and monitor the patients for any clinically relevant prolongation or shortening of the intra-ventricular delay.

The capture management features according to the invention verify that existing pacing outputs are capturing. Such tests include calculated ventricular threshold amplitude at the programmed pacing stimulus pulse width; strength duration curve showing the results with a 2× amplitude over the programmed amplitude (including the so-called safety margin); status of capture management (adaptive or monitor only); capture management parameters include some or all of the following: Ventricular Amplitude, Ventricular Pulse Width, Amplitude Margin, Pulse Width Margin, Minimum Adapted Amplitude, Minimum Adapted Pulse Width, Date when an acute phase test was completed or time remaining to next acute phase test.

The information or data gathered and used by the inventive algorithm also provides diagnostic information and trend data on the timing between the RV and LV pacing stimulus delivery and the A-RV and A-LV pacing intervals. Such timing data can be used to monitor the changes in the patient's heart conduction properties, used to detect a lead dislodgement, used to trigger a firmware-initiated PTS, and used to activate a patient alert, clinic or clinician notification or the like.

A verification test or a PTS test can be initiated by several mechanisms which include a firmware initiation, a programmer initiation and a remote monitor initiation.

In the case of a remote follow-up initiation, the clinician sets up the system to conduct a verification test followed by a PTS (if necessary) upon having a patient interrogate and download device data to a patient management-type network (e.g., the Medtronic CareLink® network). The test can be conducted asynchronously (automatically) or during an interactive remote programming session. The remote nature of the test will allow for early warning of lead issues and allow appropriate triage of patients to the EP or the Heart Failure specialist.

A template of a normal bi-v paced electrogram can be stored for template matching purposes. If the implanted device supports far-field, endocardial electrograms (EGM) or pseudo/subcutaneous ECG, a control template will also be captured from these vectors and stored far later comparison. If the QRS width is prolonged, it is likely that a capture issue exists. Periodic QRS widths can be measured by the device and if it fails out of a range defined by the control template, a firmware verification of capture can be initiated.

In an in-office programmer initiated test, similar to the remote test, the clinical user can define if a full PTS will be executed or if only a verification test will be done. This aspect of the capture management feature of the invention allows clinicians to easily conduct an in-office measurement of the pacing thresholds at each of the pacing sites.

A third case is initiation of the test via the implanted device firmware. The firmware can use a time of day approach or a detected condition from either a verification test result, the timing information, or a change in the ventricular EGM morphology (near or far-field) and QRS duration that may indicate a change in capture or a dislodgement to trigger the start of a test. A control template is stored for comparison purposes.

In the event that a remote test or a firmware-initiated test discovers a LOC event at any of the pacing sites, a patient alert will be generated via the system as is known and used in the art.

The default setting will be for the algorithm to run a verification test first and run a PTS only if indicated by the results of the verification test. The aggressiveness of the test is tiered, wherein the verification test is relatively less aggressive (e.g., by not changing any therapy delivery and only looking at sensing events) as compared to the PTS where pacing outputs are changed (at one, both or additional electrodes) while pacing can be suspended on one or the other electrodes. The sequence of tests can be programmable, thus can be set up for a different sequence as preferred by the clinician. For example, the in-office test may be a PTS only.

Once a test is initiated, the first step is to assure that the underlying conditions permit the test to run successfully. For the initial verification test that looks for sense events during bi-ventricular pacing with a few previously defined abort conditions. As the test grows in aggressiveness, new or more stringent requirements for the patient's intrinsic rhythm threshold or criteria can be required before the test begins. In general, however, the intrinsic heart rate (HR) must be low enough to permit overdrive pacing of the heart (e.g., HR at or below 100 bpm). Any detected heart rate variability (HRV) should also be of sufficiently low magnitude to allow overdrive pacing. For example, HRV can be represented as a departure from a nominal P-P, R-R interval or the like. The algorithm also should be able to define a test window that will discriminate between test beats and fusion beats. If the AV interval Is very short, or very long, premature ventricular beats may be used to allow differentiation between fusion and test pacing stimulus delivery. Also, atrial overdrive pacing may be necessary in the case of threshold testing. In the case of using EGM senses in the 40-280 ms window for confirmation, atrial overdrive pacing is likely not needed.

Once all of the predefined criteria are met, the selected test starts.

A verification test (level 1) will only confirm that capture is occurring at the currently programmed settings. It will also evaluate if a sense event can actually occur at each electrode to eliminate possible lead dislodgement as a reason for not detecting a depolarization event. Typically, the pacing outputs are not be reprogrammed nor is therapy altered as a result of this level of the test. The verification test (level 1) can be used to evaluate sense events on each of the EGMs obtained during bi-ventricular pacing, although less than all EGMs can be utilized. If there is a sense event in a window of approximately 40 to 280 ms after a bi-ventricular pacing stimulus delivery, loss of capture is suspected on the electrode that recorded the sense event. The user can then program the response of the sense system at this point to decide if a PTS is to be conducted. An alert is then set to occur in a given manner and at a given time. In an analysis of preexisting patient EGM data, the presence of a sense event within this temporal window was completely (i.e., 100%) both sensitive and specific to a lead problem related to either a higher threshold being required, LOC, or lead dislodgement from a prior operable location.

However, if an intrinsic deflection (a sensed event not resulting from pacing therapy delivery) is not detected during the bi-v portion of the test, confirmation of the ability to detect such sensed events will be sought by looking for an intrinsic deflection (a sensed event) on one of the pacing electrodes from a pace generated on the other electrode (i.e., inter-ventricular conduction) or by trying to determine if a conducted beat from the atria is detected at each of the pacing sites. The intrinsic conduction test is nominally conducted first. The AV interval is temporarily prolonged (e.g., to approximately 300 ms) and sensed events are sought. If sensing is not achievable at one of the sites, then dislodgement is suspected and an alert is set. If there is no intrinsic conduction within 300 ms, then the alternate approach of single site pacing will be used. A sensed event on one electrode will be sought from pacing at the other electrode. If no sensed event is detected, then a maximum output pace is generated at the pacing site. If no sense is yet detected, an alert is set indicating a possible lead dislodgement on the sense electrode or a possible threshold increase on the pace electrode. Each of the electrode combinations will be evaluated, if necessary or desirable. During this portion of the test there will be some temporary changes to the therapy delivered to the patient.

In the event that both electrodes show the ability to detect a sensed event (Le. no lead dislodgement) then a bi-ventricular capture is confirmed by lack of a sense in the 40-280 ms temporal window. The verification is complete. All parameters will be restored after a completion of the verification test. A bi-ventricular PTS can be conducted using the 40-280 ms sensing window as a detector for the output that fails to capture at one of the sites.

The PTS.

The PTS is an active test that seeks to define the capture threshold in either the bi-v mode or at individual electrodes.

Bi-V Test.

For a bi-ventricle test PTS, the output of both electrodes are swept at the same time and a sensed event in the LOC window on either of the electrodes would indicate the bi-V threshold. This test works best in the case where the outputs are tied together and the V-V pacing time is set to null (0).

Individual Electrodes.

In newer devices, outputs on each of the electrodes will be set individually. In this case one electrode can be used as the sensing electrode for capture at the other electrode. Other sensors can also be used such as pressure, an accelerometer, sonomicrometry, evoked response, etc. This a reasonably complex portion of the algorithm and requires a host of criteria to be met in order to have a test performed. It is in this case that a fusion window ought to be defined in order to not mistaken an intrinsic deflection as a pacing-capture event. The window of confirmation needs to take into account that a fusion contraction (or beat) is conducted from the atria. If the AV interval is very short or of the same duration as the V-V interval, a premature ventricular pace (approximately 100 ms early) can be used as the test pulse. The test pulse is optionally, but not required, preceded by a train of at least three paces. In this case, a detection of an intrinsic deflection (a sensed event) in the window of 0 ms to the expiration of the AV interval from a pace on the other electrode indicates a capture confirmation. An output sweep conducted until a LOC is detected. The pacing output of last capture is recorded and the output of that electrode is set to that value plus, optionally, a safety margin. The second electrode has the same test performed on it as just described. During this portion of the search, the atrium would be paced at the same time as the ventricles in order to increase the detection window size and reduce the likelihood of a conducted beat from the atrium being sensed as a successful capture on one of the ventricular leads. Timing information related to the conduction time between electrodes can be stored by the device and used for reporting patient myocardial conduction status. Trends of these conduction times will be maintained in order to detect any clinically important changes in the patient's myocardial conduction properties.

The PTS described herein allows for temporary alteration of bi-ventricular pacing during performance of the PTS, pacing at one of the ventricular sites will be turned off while the output sweep on the other electrode is conducted.

A premature V test pace can be used if the AV interval is of the same duration as the V-V interval. The capture detector can be evoked response if this circuitry is available in the device or it can be the sensing of an intrinsic deflection on the other ventricular electrode combined with the appropriate timing information which takes into account any conducted beats from the atrium. Capture detectors can range from the evoked response detector, the intrinsic deflection on another vector or electrode, pressure changes due to a contraction, accelerometer disposed on or about one or both ventricles, piezoelectric crystal, intra-cardiac impedance, sonomicrometry, or any sensor which can detect a mechanical or electrical activation.

As mentioned, a PTS test can also be triggered by the clinician during an in-office evaluation and in this case the verification test can be bypassed.

At least in part, some of the novel features of this present invention relate to using the other electrode as a means to confirm capture on the first electrode. The technique also uses an algorithmic approach to sense and verify capture with different level tests which have an increasing level of aggressiveness and intervention.

The particular operating mode of the present invention is a programmed or hard-wired sub-set of possible CRT delivery operating modes, including bi-ventricular pacing whether involving simultaneous V-V pacing stimulation (i.e., synchronized ventricular pacing therapy delivery) or offset V-V pacing stimulation (e.g., in an attempt to compensate for various cardiac conduction and/or contractile defects). In addition, the invention can be used to verify pacing capture of either one of an RV or an LV (and RA and LA). As noted, the inventive algorithm advantageously helps confirm the capture status of a pacing regimen by providing one of: a LOC signal, a capture signal, or a "capture suspect" signal. Of course, the methods according to the present invention are intended to be stored as executable instructions on any appropriate computer readable medium that provides control signals to effect the technical result of the invention herein described and depicted, although certain of the steps of the inventive methods may be performed manually as well.

In the presently described and depicted embodiment of the invention capture verification testing occurs on a daily basis, however, the testing may occur based on a triggering signal (e.g., from a patient or clinician, from a hand-held programmer or the like locally or remotely spaced from said patient). Upon confirmation of capture of a cardiac chamber, a desired pacing therapy delivery can be re-enabled and continue until: a loss of capture occurs, a predetermined period of time elapses, a mode-switch occurs to another pacing regimen (e.g., due to a automated physiologic trigger, a programming change, etc.) or the like. If a loss of capture in a ventricular chamber is detected it could indicate one or more possible problems requiring remedial action. For example, the pacing stimulus might be arriving too late (e.g., during the refractory period of the chamber), the pacing electrodes might have malfunctioned or become dislodged, an elongated conductor within a medical electrical lead might have been damaged, open- or short-circuited. Accordingly, in addition to verifying pacing capture, the present invention optionally includes capability for alerting a physician, clinician, patient, health care provider or the like that pacing system interrogation might be required. In addition, the configuration of the pacing system, including collected patient data and physiologic parameters can be stored for later retrieval thereby enhancing the likelihood of an accurate assessment of the operating condition of the pacing system.

In one form of the invention, following detection of inappropriate or non-programmed operating conditions (e.g., including receipt of a LOC signal during CRT delivery) the pacing therapy can be adjusted, discontinued or a mode switch performed to another pacing modality which, for example might exclude the pacing lead that produced the LOC signal.

One aspect of this form of the invention, upon receipt of a ventricular LOC signal an intended bi-ventricular or uni-ventricular CRT delivery regimen is suspended and an atrial-pacing only therapy is implemented (e.g., an AAI, ADI, AAI/R, ADI/R and the like). That is, assuming that a patient's A-V conduction remains relatively intact until such time as the patient is able to receive qualified medical attention or until a subsequent ventricular capture verification test indicates that non-suspect capture has been achieved. In this regard, U.S. Pat. No. 6,772,005 to Casavant et al. entitled "Preferred ADI/R: a Permanent Pacing Mode to Eliminate Ventricular Pacing While Maintaining Backup Support" which is assigned to Medtronic, Inc. is hereby incorporated herein by reference in its entirety.

In addition, the present invention can operate in non-tracking modes wherein for example, with a patient at rest (based on a nominal activity sensor signal) a supraventricular tachycardia (SVT) episode occurs. The SVT episode causes the atrial channel of a dual-chamber IPG to sense a rapid (atrial) rate while the input to ventricular sensor(s) indicates physical inactivity and therefore no need to increase the pacing rate. The pacemaker can use this information to make the diagnosis of SVT and activate automatic mode switching to a nontracking mode (to control the paced ventricular rate). Thus, the PTS and verification testing can occur without relying on a stable HR, although the abort criteria typically will preclude the operation of the PTS and verification testing absent a stable HR and absence of HRV.

The patient may, in the best scenario, be relieved of pacing therapy delivery altogether (programming the pacing circuitry to an ODO monitoring-only "pacing modality"). Assuming the patient is not chronotropically incompetent, normal sinus rhythm may emerge permanently for all the activities of daily living. Additionally, the process 600 may be employed to search for a change in conduction status (e.g., wherein a later-to-depolarize ventricle changes from the LV to the RV).

A few salient features of the automatic, ambulatory LV/RV capture verification test according to the invention are described below:

(1) The feature (e.g., "Automatic LV/RV Capture Verification") will be selectably programmable by the user and no other programmable parameters associated with the conduction test sequences.

(2) A "patient alert" type selection can be optionally provided (selectable on or off) associated with the results of the LV/RV Capture Verification test sequences. Such an alert feature includes a range of selectable options regarding when to sound the alert (e.g., immediately after a negative test, based on diurnal cycles such as in the morning or upon detection of patient activity after a lengthy sedentary period, etc.) are within the purview of the invention.

(3) In one form of the invention, the conduction test sequences are applied at approximately the same (whether on a daily-, weekly-, monthly-basis, etc.) for example at night when the patient is sleeping. For the example described, the tests are applied at 3:00 a.m.

(4) The conduction test sequence with generally be withheld in the event that the patient's then-current heart rhythm supports running the test (e.g., no atrial or ventricular tachycardia episodes in progress at the time when the test starts or while the test sequences are running, the atrial rate is relatively low, and the patient is currently paced in the ventricle).

(5) For example, every night at approximately 3:00 a.m. the device initiates the conduction test sequence. The first step is to measure the time interval between an atrial event to an antegrade-conducted RV sense (referred to as "PR interval" herein). This is done by setting a relatively long AV interval (e.g., 400 ms) for one cardiac cycle and measuring the time between said A-event and the associated v-event (i.e., an RV sensed event). If a ventricular pace (VP) occurs, it indicates that the patient likely has some degree of AV block. The PR interval used for an algorithm according to the invention (see below) will be set to the programmed AV interval in this case.

(6) The device is then programmed to LV-only pacing for one cardiac cycle with a relatively short, or minimum, AV interval. Then, one of the following two results are obtained, with the concomitant response(s).

a. No sense RV-event: If an RV-event is not sensed prior to the next scheduled ventricular pace (VP), it implies "loss of capture" (LOC) because there is no conduction from the LV paced event to the RV—assuming that RV sensing components and circuitry are not an issue. For completeness, other cardiac pacing system features are available and will be provided to alert the clinician to this possibility (but such features are not relevant to the present invention). However, the inventors posit that there exists a rare possibility that a premature ventricular contraction (PVC) may have occurred around the time of the LV pace event (pacing stimulus delivery to the LV) in which case no RV sense event can occur due to the LV pace event (and, in particular, the associated sensing-channel blanking typically imposed upon delivery of the LV pacing stimulus). To address this unlikely situation step (6) is again performed. If an RV sense event is still not recorded, then a "loss of capture" (LOC) output signal is issued as the test result. If an RV-sense event is recorded, then the method proceeds to option b. (immediately below).

b.) RV sense event recorded: If an RV sense event is recorded prior to the next LV pace, it could mean that it came from (A) an intrinsically-conducted PR interval (from an A-event), or (B) a conducted inter-ventricular event (i.e., a conducted LV pace event that conducts to the RV), or (C) a PVC.

i.) Criteria for recording a relatively 'early' RV sense event: If the time interval from an A-event to an R-sense event (referred to herein as a "Test PR") is less than or equal to the PR Interval less about 40 milliseconds (i.e., PR Interval—40 ms), then the event could either represent scenario (B) or (C) above. In this situation, step (6) is again repeated. If the just-described pattern manifests itself again, then ventricular pacing capture is verified (i.e., case (B) is confirmed). Such a verification and confirmation appears reasonable because the likelihood that a PVC might occur again at the same exact time interval is highly unlikely and can be safely ignored. However, if the pattern is not repeated again, then the prior RV-sensed event in fact represents a PVC and the current A event to RV sense interval requires attention by applying the following criteria and steps.

ii.) Criteria for recording of an "on time" RV sense event: If an RV sense event is recorded prior to the next LV pace (on the same cardiac cycle) and the Test PR interval is greater than the PR Interval less 40 milliseconds (i.e., PR Interval—40 ms), then the RV sense event comprises either: (A) a situation wherein the LV has lost pacing capture (LOC) or (A') where the LV-RV inter-ventricular interval is greater than the PR interval or (B) a situation wherein the LV-RV inter-ventricular interval is approximately the same as the PR interval. Since the inventors recognize that empirically (i.e., from data gathered from the MIRACLE ICD trial) data has shown that interventricular intervals (e.g., LVP to RVS interval) times are rarely, if ever, greater than about 280 milliseconds.

Applying these values, then in the event that the Test PR is greater than 310 ms (i.e., equal to the programmed AV delay interval plus the LVP-RVS interventricular conduction time), then the result of the conduction test is a "loss of capture" (LOC) conclusion.

Conversely, if the Test PR is less than or equal to 310 milliseconds then the results of the conduction test is a "capture is suspect." Both the PR Interval and the Test PR Interval are then optionally stored into a histogram, a trend log or the like.

(7) If the result of the conduction test sequence is "capture is suspect," then the recent or previous recorded history of the patient can be used to determine if the loss of capture (LOC) result is more or less likely. Accordingly, if ventricular capture has been verified in the recent past and the presently applied Test PR Interval is much larger than previous Test PR Interval (e.g., on the order of about 60 ms larger or different, then "loss of capture" (LOC) is the result of the conduction test sequence.

(8) If a patient alert feature has been programmed to issue upon an LOC result, then an alert will be sounded at the programmed time. Such a patient alert can comprise any of a variety of apparatus and circuitry intended to gain the attention of a patient. Some examples include a haptic or vibratory alert wherein a crystal or other structure disposed within an implantable medical device oscillates or moves, an audible alert, and/or activation of visual cues signaling an alert event. The alert message can be sent wirelessly to remote stations or adjacent hardware so that the patient and/or other personnel also receive the alert message.

(9) the foregoing steps (5) through (7) can be repeated every night or on an otherwise periodic or aperiodic basis.

Some of the key elements of the inventive algorithm just described are depicted and described with reference to an exemplary embodiment shown in the flowchart appended hereto (e.g., FIG. 4). The exemplary embodiment illustrates LV capture verification and pacing threshold search (PTS) testing. Of course, a similar flowchart also applies for RV capture verification (e.g., by switching to RV-only pacing in lieu of LV-only pacing) and can be applied for at least one cardiac cycle. The inventive conduction test sequence can be run during atrial overdrive pacing. Such overdrive pacing is known in the art and results in an increase of the length of the interval between a preceding A-event and an associated, conducted V-sense event.

Figure 4:
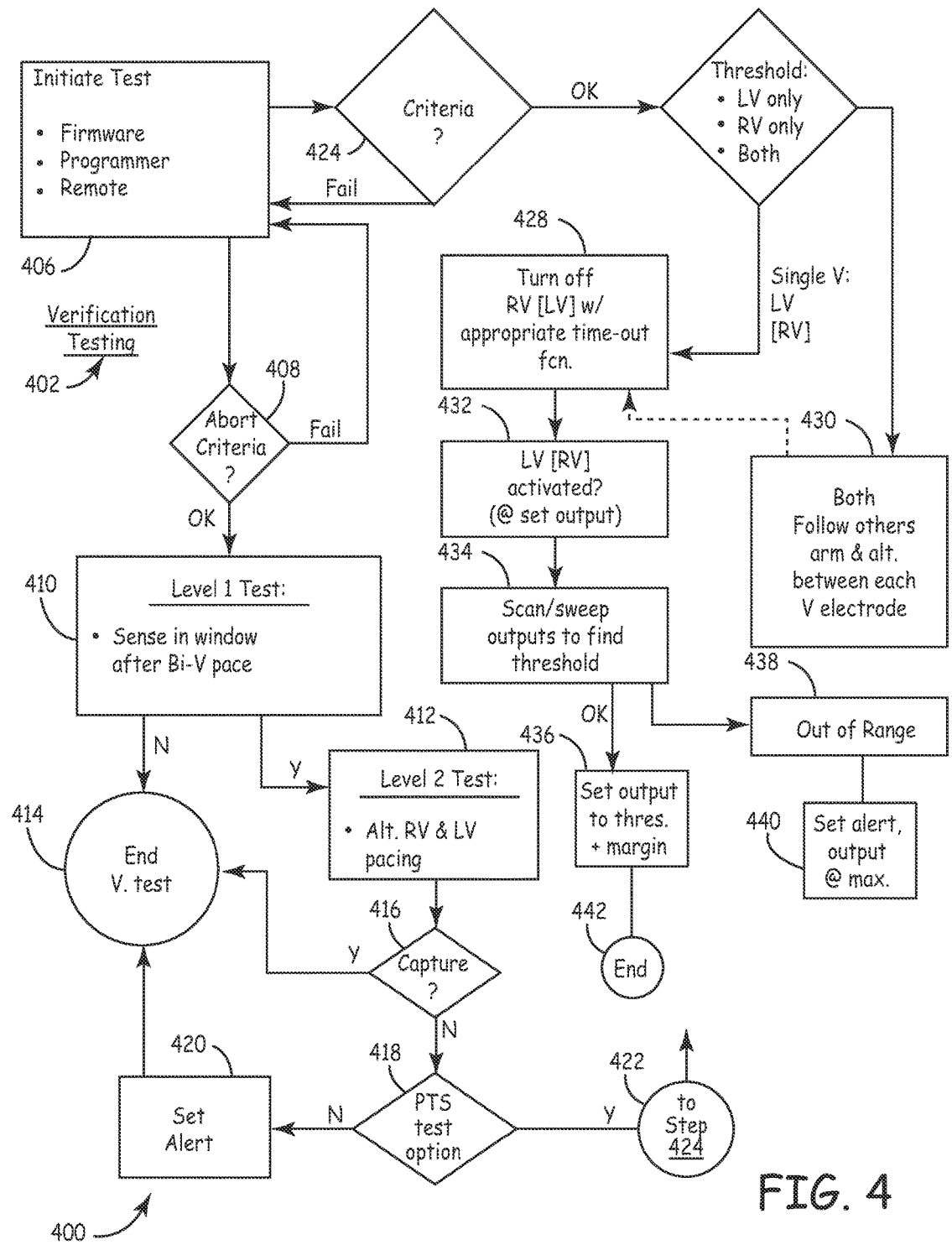
FIG. 4 is a flow chart depicting an embodiment of ventricular capture verification and pacing threshold testing regimen according to the present invention

Now referring to FIG. 4, a method 400 according to an embodiment of the invention is depicted. The method 400 includes two major paths or branches; namely verification testing 402 and the PTS test 404.

With respect to verification testing 402, following a test initiation step 406 wherein the various components of a system for carrying out the invention are checked (e.g., the operative firmware and/or software, the device programming instrument for wirelessly communicating with an implantable medical device such as a CRT delivery platform, any remote communication links, etc.). Following step 406 the test module 402 of method 400 enters decision step 408 wherein certain test abort criteria are checked. As noted herein the abort criteria can include a variety of items which ought to be satisfied before the test module 402 can proceed. However, the abort criteria can depend at least in part on whether the test is being triggered remotely (e.g., via the Medtronic CareLink® network) or in a clinic-type setting. In addition, if the test module 402 occurs in a nontracking CRT mode or pacing mode (i.e., a mode which essentially ignores atrial events, usually due to the presence of a high rate atrial tachycardia such as a supraventricular tachycardia or SVT). If the abort criteria causes a failure the test module 402 can revert to the initiate test step 406 with re-attempts to perform the test module 402 thereafter on a periodic basis. If the abort criteria does not cause a failure then at step 410 a primary, or level I, test occurs. In the level I test substantially simultaneous bi-ventricular pacing therapy is provided to each ventricle and each ventricle is monitored for evoked activation during a window of time that reveals whether the dual pacing stimulation captured both ventricles. The window is nominally set of approximately 40 ms to about 280 ms and assuming no sensed, or detected, ventricular events during that window the result of step 410 is negative and the verification test ends at 414. If step 410 results in a sensed ventricular event during the window then the level I test is affirmative and a level II test commences at step 412.

In the level II test alternating LV and RV pacing stimulation is provided (at relatively short AV intervals) while the non-paced ventricle is monitored for inter-ventricular conduction, which indicate capture of the paced ventricle. If capture is declared at step 416 then the test ends at step 414. If LOC is declared (or suspect capture is declared), then at step 418 an optional PTS test is invoked (at step 424). If the optional PTS test is declined then an alert is set at step 420 and the test ends at step 414. The alert can include all relevant present and/or prior verification testing details and the settings of the IPG and patient information, and the like.

Following or in lieu of performing verification test module 402, a PTS test module 404 can be performed beginning with a preset abort (test) criteria step at 424. As before, if the PTS module 404 fails at 424 then the PTS test can be re-attempted or retried at a later time. Assuming that abort criteria 424 are not satisfied then an iterative threshold testing regimen begins at step 426 wherein both or just one of the RV and LV can be tested to provide a pacing threshold of sufficient energy to capture the RV and/or LV. If just one of the LV or RV is to be tested then at step 428 the pacing stimulation to the non-threshold testing ventricle is turned off (with an appropriate time-out function). If both the LV and the RV are to be tested then at step 430 the process flow causes steps 428-442 to be performed serially (for each ventricle). As depicted, in FIG. 4 the process flow for LV threshold testing is illustrated (with the RV shown in brackets [RV] to indicate the switch for RV threshold testing. At step 432 for LV [RV] testing at the then-present pacing energy threshold the RV is monitored for activation of the LV. If the LV activates then at step 434 the pacing energy is decremented until LOC is declared and then increased until capture is restored in an iterative series of cardiac cycles. The decrement (or increment) can include any reasonable magnitude of energy and can include one or more of pulse width, pulse amplitude, polarity, frequency, and the like. In one embodiment the pulse amplitude is incremented and each increment or decrement equals a nominal 0.5V.

The so-called scan/sweep of pacing energy thus provides a pacing threshold for one or both ventricles. The pacing energy can differ between the ventricles due to a number of physiologic and pacing electrode conditions. If step 434 fails to provide a pacing threshold with a cognizable value then an out-of-range message is logged and/or communicated at step 438 and an alert is set and pacing output set to a maximum allowable value at step 440. On the other hand, if the step 432 provides in-range values for pacing thresholds for the LV and/or RV then at step 436 the pacing output is set to a value (that can optionally include a so-called safety margin) for chronic pacing therapy delivery and the PTS module 404 ends at step 442.

In addition, a programmable bi-ventricular parameter defining V-V conduction time can be supplied to and used by the inventive algorithm. Such a conduction time can be set to a worst-case default value (e.g., 280 ms), and thereafter be user-adjusted or programmable by the user or clinician to render the test results more determinate for patients with relatively "shorter" PR intervals and relatively "longer" V-V intervals.

Devices incorporating the methods according to the invention can advantageously store and display trend, histogram and/or other information regarding capture verification tests, failing test results and results for the last few months and other data related thereto. When such data is displayed in a histogram format a clinician or patient can perhaps more readily comprehend the meaning of the data, so this type of display is favored, especially for patient display. This data would be transmitted over a hospital-, clinic-, and/or patient-adapted information network (e.g., such as the Medtronic Medtronic CareLink® network) with triggers and alerts triggered by 'Capture Verification Suspect" and LOC results to alert one or more clinicians viewing the patient data remotely.

The same algorithm can be adapted slightly and advantageously applied for easy-to-use in and a clinic or physician office to verify LV and RV capture or to facilitate ambulatory LV and RV capture management (e.g., if ventricular capture is deemed to be "lost," the same algorithm is then applied at different pacing output strength to automatically determine, and program, a new pacing output at which assures ventricular pacing capture).

It should be understood that, certain of the above-described structures, functions and operations of the pacing systems of the illustrated embodiments are not necessary to practice the present invention and are included in the description simply for completeness of an exemplary embodiment or embodiments. It will also be understood that there may be other structures, functions and operations ancillary to the typical operation of an implantable pulse generator that are not disclosed and are not necessary to the practice of the present invention. In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of monitoring and/or adjusting therapy delivery via a ventricular cardiac resynchronization therapy (CRT) delivery device, comprising:

monitoring at least one of an atrial-left ventricular (A-LV) interval, an atrial-right ventricular (A-RV) interval, a LV to RV interval;

storing in a memory structure said at least one of the A-LV interval, the A-RV interval, the left ventricular (LV) to right ventricular (RV) interval (LV-RV);

performing a temporal trend analysis upon said at least one of the foregoing stored intervals over a discrete period of time, utilizing a plurality of discrete values of said stored intervals; and performing an automated ventricular chamber capture management pacing threshold test for the LV and the RV, wherein the capture management pacing threshold test comprises delivering pacing pulses and further a comprises a determination that the delivered pacing pulses were effective to capture only one of the LV and RV and of which of the LV and RV the delivered pacing pulses were effective to capture.

2. A method according to claim 1, A method of monitoring and/or adjusting therapy delivery via a ventricular cardiac resynchronization therapy (CRT) delivery device, comprising:

monitoring at least one of an atrial-left ventricular (A-LV) interval, an atrial-right ventricular (A-RV) interval, a LV to RV interval;

storing in a memory structure said at least one of the A-LV interval, the A-RV interval, the left ventricular (LV) to right ventricular (RV) interval (LV-RV);

performing a temporal trend analysis upon said at least one of the foregoing stored intervals over a discrete period of time, utilizing a plurality of discrete values of said stored intervals; and performing an automated ventricular chamber capture management pacing threshold test for the LV and the RV, wherein the capture management pacing threshold test comprises delivering pacing pulses and further a comprises a determination of which of the LV and RV the delivered pacing pulses were effective to capture;

wherein said trend analysis includes one of: a percentage of time wherein at least one of the LV and the RV were deemed to have loss of capture (LOC), a percentage of time when one of the LV and the RV were deemed to have successfully captured, a percentage of time when one of the LV and the RV were deemed to have unknown or uncertain capture status.

3. A method according to claim 1, wherein said capture management pacing threshold test further comprises:

delivering bi-ventricular pacing therapy for at least one cardiac cycle; and sensing in at least one of the LV and the RV for a latent ventricular event indicative of loss of capture in one of said LV and RV.

4. A method according to claim 3, wherein an LV-RV interval used to deliver the bi-ventricular pacing therapy comprises a substantially null value.

5. A method according to claim 3, wherein said sensing for said latent ventricular event occurs during a temporal window about 40 milliseconds (ms) to 280 ms subsequent to the delivery of the bi-ventricular pacing therapy and further comprising:

declaring one of loss of capture (LOC) and suspected cardiac lead dislodgement in each of the LV and RV that recorded the latent ventricular event during the temporal window.

6. A method according to claim 3, wherein said sensing for said latent ventricular event occurs during a window about 40 milliseconds (ms) to 280 ms subsequent to the delivery of the bi-ventricular pacing therapy and further comprising:

declaring capture in each chamber that failed to record the latent ventricular event during the temporal window.

7. A method according to claim 3, further comprising independently adjusting the pacing energy of one of the LV and RV so that each of the LV and RV capture during bi-ventricular pacing therapy delivery.

8. A method according to claim 6, further comprising in the event that a latent sense does not occur, then performing one of the following to establish that a sensed event would have occurred in the event of loss of capture; namely:

performing one of: a. delivering bi-ventricular pacing therapy having a prolonged A-RV interval or A-LV interval to verify the occurrence of atrio-ventricular conduction; b. delivering single ventricular pacing therapy with a shortened A-RV or A-LV interval to verify the occurrence of inter-ventricular conduction and c. delivering a premature ventricular pacing stimulus to a first ventricle in lieu of a shortened A-RV or A-LV interval to verify the occurrence of inter-ventricular conduction if the stimulus captures; and declaring capture only if both atrio-ventricular conduction and inter-ventricular conduction are verified.

9. A method according to claim 5, further comprising:

performing a pacing threshold search by one of incrementing an decrementing the magnitude of pacing energy delivery until pacing capture is confirmed at both the LV and the RV; and performing at least one of storing information regarding the confirmed pacing capture and communicating to a remote patient management network regarding the confirmed pacing capture.

10. A method according to claim 9, further comprising storing the value of the magnitude of pacing energy used to confirm capture in each of said LV and the RV in a computer memory.

11. A method according to claim 9, further comprising incrementing the pacing energy level a predetermined amount and chronically delivering pacing therapy at said incremented pacing energy level.

12. An apparatus for monitoring, delivering and/or adjusting cardiac therapy delivery, comprising:

means for monitoring at least one of an atrial-left ventricular (A-LV) interval, an atrial-right ventricular (A-RV) interval, a left ventricular (LV) to right ventricular (RV) interval;

means for storing in a memory structure said at least one of the A-LV interval, the A-RV interval, the LV to RV interval;

means for performing a temporal trend analysis upon said at least one of the foregoing stored intervals over a discrete period of time, utilizing a plurality of discrete values of said stored intervals; and means for performing an automated ventricular chamber capture management pacing threshold test for at least one of the LV and the RV, wherein the capture management pacing threshold test comprises delivering pacing pulses and further a comprises a determination that the delivered pacing pulses were effective to capture only one of the LV and RV and of which of the LV and RV the delivered pacing pulses were effective to capture.

13. An apparatus according to claim 12, wherein said automated threshold test is triggered by one of: a clinician, a relatively longer duration QRS complex, a morphologically relatively different QRS complex.

14. An apparatus according to claim 13, wherein said trend analysis includes one of: a percentage of time wherein at least one of the LV and the RV were deemed to have loss of capture (LOC), a percentage of time when one of the LV and the RV were deemed to have successfully captured, a percentage of time when one of the LV and the RV were deemed to have unknown or uncertain capture status.

15. An apparatus according to claim 13, further comprising:
    means for delivering bi-ventricular pacing therapy for at least one cardiac cycle; and
    means for sensing in at least one of the LV and the RV for a latent ventricular event indicative of loss of capture in one of said LV and RV.

16. An apparatus according to claim 15, wherein an LV-RV interval used to deliver the bi-ventricular pacing therapy comprises a substantially null value.

17. An apparatus according to claim 15, wherein said sensing for said latent ventricular event occurs during a temporal window about 40 milliseconds (ms) to 280 ms subsequent to the delivery of the bi-ventricular pacing therapy and further comprising:
    declaring one of loss of capture (LOC) and suspected cardiac lead dislodgement in each of the LV and RV that recorded the latent ventricular event during the temporal window; and
    performing a pacing threshold search for each of the LV and RV that recorded the latent ventricular event during the temporal window.

18. An apparatus according to claim 15, wherein said sensing for said latent ventricular event occurs during a window about 40 milliseconds (ms) to 280 ms subsequent to the delivery of the bi-ventricular pacing therapy and further comprising:
    declaring capture in each chamber that failed to record the latent ventricular event during the temporal window.

19. An apparatus according to claim 15, further comprising means for independently adjusting the pacing energy of one of the LV and RV so that each of the LV and RV capture during bi-ventricular pacing therapy delivery.

20. A method of monitoring and/or adjusting therapy delivery via a ventricular cardiac resynchronization therapy (CRT) delivery device, comprising:
    monitoring at least one of an atrial-left ventricular (A-LV) interval, an atrial-right ventricular (A-RV) interval, a LV to RV interval;
    storing in a memory structure said at least one of the A-LV interval, the A-RV interval, the left ventricular (LV) to right ventricular (RV) interval (LV-RV); and
    performing an automated ventricular chamber capture management pacing threshold test for the LV and the RV, wherein the capture management pacing threshold test comprises delivering pacing pulses and further a comprises a determination that the delivered pacing pulses were effective to capture only one of the LV and RV and of which of the LV and RV the delivered pacing pulses were effective to capture.

21. A method according to claim 20, wherein said capture management pacing threshold test further comprises:
    delivering bi-ventricular pacing therapy for at least one cardiac cycle; and
    sensing in at least one of the LV and the RV for a latent ventricular event indicative of loss of capture in one of said LV and RV.

22. A method according to claim 21, wherein an LV-RV interval used to deliver the bi-ventricular pacing therapy comprises a substantially null value.

23. A method according to claim 21, wherein said sensing for said latent ventricular event occurs during a temporal window about 40 milliseconds (ms) to 280 ms subsequent to the delivery of the bi-ventricular pacing therapy and further comprising:
    declaring one of loss of capture (LOC) and suspected cardiac lead dislodgement in each of the LV and RV that recorded the latent ventricular event during the temporal window.

24. A method according to claim 21, wherein said sensing for said latent ventricular event occurs during a window about 40 milliseconds (ms) to 280 ms subsequent to the delivery of the bi-ventricular pacing therapy and further comprising:
    declaring capture in each chamber that failed to record the latent ventricular event during the temporal window.

25. A method according to claim 21, further comprising independently adjusting the pacing energy of one of the LV and RV so that each of the LV and RV capture during bi-ventricular pacing therapy delivery.

26. A method according to claim 25, further comprising in the event that a latent sense does not occur, then performing one of the following to establish that a sensed event would have occurred in the event of loss of capture; namely:
    performing one of: a. delivering bi-ventricular pacing therapy having a prolonged A-RV interval or A-LV interval to verify the occurrence of atrio-ventricular conduction; b. delivering single ventricular pacing therapy with a shortened A-RV or A-LV interval to verify the occurrence of inter-ventricular conduction and c. delivering a premature ventricular pacing stimulus to a first ventricle in lieu of a shortened A-RV or A-LV interval to verify the occurrence of inter-ventricular conduction if the stimulus captures; and
    declaring capture only if both atrio-ventricular conduction and inter-ventricular conduction are verified.

27. An apparatus for monitoring, delivering and/or adjusting cardiac therapy delivery, comprising:
    means for monitoring at least one of an atrial-left ventricular (A-LV) interval, an atrial-right ventricular (A-RV) interval, a left ventricular (LV) to right ventricular (RV) interval;
    means for storing in a memory structure said at least one of the A-LV interval, the A-RV interval, the LV to RV interval; and
    means for performing an automated ventricular chamber capture management pacing threshold test for at least one of the LV and the RV, wherein the capture management pacing threshold test comprises delivering pacing pulses and further a comprises a determination that the delivered pacing pulses were effective to capture only one of the LV and RV and of which of the LV and RV the delivered pacing pulses were effective to capture.

28. An apparatus according to claim 13, further comprising:
    means for delivering bi-ventricular pacing therapy for at least one cardiac cycle; and
    means for sensing in at least one of the LV and the RV for a latent ventricular event indicative of loss of capture in one of said LV and RV.

29. An apparatus according to claim 28, wherein an LV-RV interval used to deliver the bi-ventricular pacing therapy comprises a substantially null value.

30. An apparatus according to claim 28, wherein said sensing for said latent ventricular event occurs during a temporal window about 40 milliseconds (ms) to 280 ms subsequent to the delivery of the bi-ventricular pacing therapy and further comprising:

declaring one of loss of capture (LOC) and suspected cardiac lead dislodgement in each of the LV and RV that recorded the latent ventricular event during the temporal window; and performing a pacing threshold search for each of the LV and RV that recorded the latent ventricular event during the temporal window.

31. An apparatus according to claim 28, wherein said sensing for said latent ventricular event occurs during a window about 40 milliseconds (ms) to 280 ms subsequent to the delivery of the bi-ventricular pacing therapy and further comprising:

declaring capture in each chamber that failed to record the latent ventricular event during the temporal window.

32. An apparatus according to claim 28, further comprising means for independently adjusting the pacing energy of one of the LV and RV so that each of the LV and RV capture during bi-ventricular pacing therapy delivery.

\* \* \* \* \*